United States Patent [19]
Budovich et al.

[11] Patent Number: 5,969,349
[45] Date of Patent: Oct. 19, 1999

[54] ION MOBILITY SPECTROMETER

[75] Inventors: Vitali Lvovich Budovich; Alexei Anatolevich Mikhailov, both of Moscow, Russian Federation; Gerd Arnold, Leipzig, Germany

[73] Assignee: Bruker-Saxonia Analytik GmbH, Leipzig, Germany

[21] Appl. No.: 08/890,399

[22] Filed: Jul. 9, 1997

[30]      Foreign Application Priority Data

Jul. 9, 1996  [DE]   Germany ................ 196 27 621

[51] Int. Cl.⁶ ............................................ H01J 49/00
[52] U.S. Cl. ............................................ 250/286
[58] Field of Search .................... 250/286, 287, 250/281, 282

[56]          References Cited

U.S. PATENT DOCUMENTS 5,021,654   6/1991   Campbell et al. ............... 250/287
5,587,581  12/1996   Stroosnyder .................... 250/287

FOREIGN PATENT DOCUMENTS 0198154  10/1986   European Pat. Off. .

OTHER PUBLICATIONS

P. Begley et al., *Photoemissive ionization source for ion mobility detectors*, Journal of Chromatography, vol. 588, pp. 239–249, 1991.

*Primary Examiner*—Kiet T. Nguyen

[57]              ABSTRACT

Ion mobility spectrometer with a non-radioactive electron source to generate ions inside a reaction chamber. The reaction chamber consists of two partial chambers, one of which is evacuated and comprises the electron source, and the other one is connected to the drift chamber of the IMS via a shutter grid. The partition wall between both partial chambers is transparent to electrons but impermeable for gas molecules. The electron source may comprise a thermoemitter or a photocathode, which is illuminated from outside through a window. In this way, any contact between analyte and electron source is avoided, thereby improving the measuring stability and enabling operation in positive and negative mode.

13 Claims, 2 Drawing Sheets

ION MOBILITY SPECTROMETER

FIELD OF THE INVENTION

The present invention relates to analysis of the impurities in a gas and more particularly to an ion mobility spectrometer to perform a corresponding analysis.

BACKGROUND OF THE INVENTION

Ion mobility spectrometers (IMS) came into being in the early 1970's in order to analyze and detect organic vapors in air. An ion mobility spectrometer consists of a reaction chamber for the generation of ions of substances to be analyzed and a drift chamber for separation of the ions. In the reaction chamber, for ionization of the substance to be analyzed, usually radioactive materials such as, for example, tritium, $^{53}$Ni, $^{241}$Am etc. are used. The disadvantage of such IMS is that the use of a radioactive ionization source can be dangerous to the environment and to the health of maintenance personal.

In this context there were made numerous attempts to design IMS constructions with non-radioactive ionization sources in the reaction chamber such as, for example, photoemitter to generate electrons. However, in these designs one could not exclude the contact of analyzed gas molecules with the source surface. This is one of the reasons for instabilities of detector indications because such contacts can change the operating characteristics of a non-radioactive source.

The prior art IMS consist of a reaction chamber, a drift chamber, a non-radioactive electron source installed in said reaction chamber, an input connected to said reaction chamber for supplying an analyte and an output for withdrawing said analyte, as well as a collecting electrode mounted in said drift chamber (ref. e.g. Begley P., Carbin R., Fougler B. F., Sammonds P. G., J. Chromatogr. 88 (1991) p. 239).

The disadvantage of these prior art IMS is that the analyte directly contacts the surface of the non-radioactive ionization source which in its turn changes the operating characteristics of said ionization source and may be one of the reasons for the instability of detector indications. Another disadvantage is that one cannot obtain positive ions with the help of such an ionization source.

The purpose of this invention lies in the design of an IMS construction that eliminates the contact of the analyte with the ionization source and enables one to work with positive and negative ions.

SUMMARY OF THE INVENTION

Said purpose is achieved by an IMS with a reaction chamber, a drift chamber, a non-radioactive electron source mounted in said reaction chamber, an input for supplying an analyte to the reaction chamber and an output for withdrawing said analyte, as well as a collecting electrode mounted in said drift chamber, wherein the reaction chamber is divided into two partial chambers by a partition wall permeable to the electrons and not permeable to gas, wherein a non-radioactive electron source is mounted in the first partial chamber and the second partial chamber is coupled to the input for supplying, and to the output for withdrawing, gas and wherein the inner volume of the first partial chamber is evacuated and said electron source is connected to a negative terminal of an accelerating voltage source.

In this way the object is completely achieved.

Since the electron source is housed in a separate, evacuated chamber, each contact of the gas with its surface is avoided and constant, controlled operating conditions prevail all the time. On the other hand, the electron transparency of the partition wall enables them to enter the second partial chamber of the reaction chamber, which is part of the IMS gas circuit whereby molecule ions for the positive and negative operation mode of the IMS are formed by reaction of the electrons entering through the partition wall with the gas molecules.

In the preferred embodiment of the invention the partition wall dividing the reaction chamber into two parts is made from mica. This is a particularly suited material with on the one hand high electron transparency being on the other hand sufficiently gas tight.

In order to avoid any possible bending of the partition wall due to pressure differences, it is supported by a metal grid (e.g. copper) with low scattering and absorption coefficients for electrons.

The surface of the partition wall is preferably coated by a layer of conductive material connected to a positive terminal of an accelerating voltage source. In this way, the electrons can be accelerated towards the partition wall and penetrate it afterwards.

In one possible embodiment of the invention the non-radioactive electron source consists of a thermoemitter supplied by a heater voltage source.

In another embodiment of the invention the non-radioactive electron source is a photocathode; whereby the part of the reaction chamber with the electron source has a window made from a material permeable to radiation. Outside the reaction chamber a radiation source, preferably a UV lamp is mounted directly opposite said window.

Preferably the window material consists of UVvol and the UV lamp emits across the spectral range from 220 nm to 400 nm.

A preferred embodiment of the proposed spectrometer is further characterized in that between the electron source and the partition wall there is an additional accelerating electrode which is connected to the accelerating voltage source.

The above features of the proposed spectrometer completely eliminate any contact between analyte and working surface of the non-radioactive electron source, thereby improving the stability of spectrometer measurements.

Further advantages of the invention will appear from the specification and the attached drawing. It is understood that the features that have been mentioned before and will be described hereafter may be used not only in the stated combinations but also in any other combination or individually, without departing from the scope of the present invention. The embodiments described are not to be considered as exhaustive enumeration but rather have exemplary character only.

BRIEF DESCRIPTION OF THE DRAWINGS

The invention is represented in the drawings and is further described with reference to detailed embodiments. It is shown.

DESCRIPTION OF THE PREFERRED EMBODIMENTS

Figure 1:
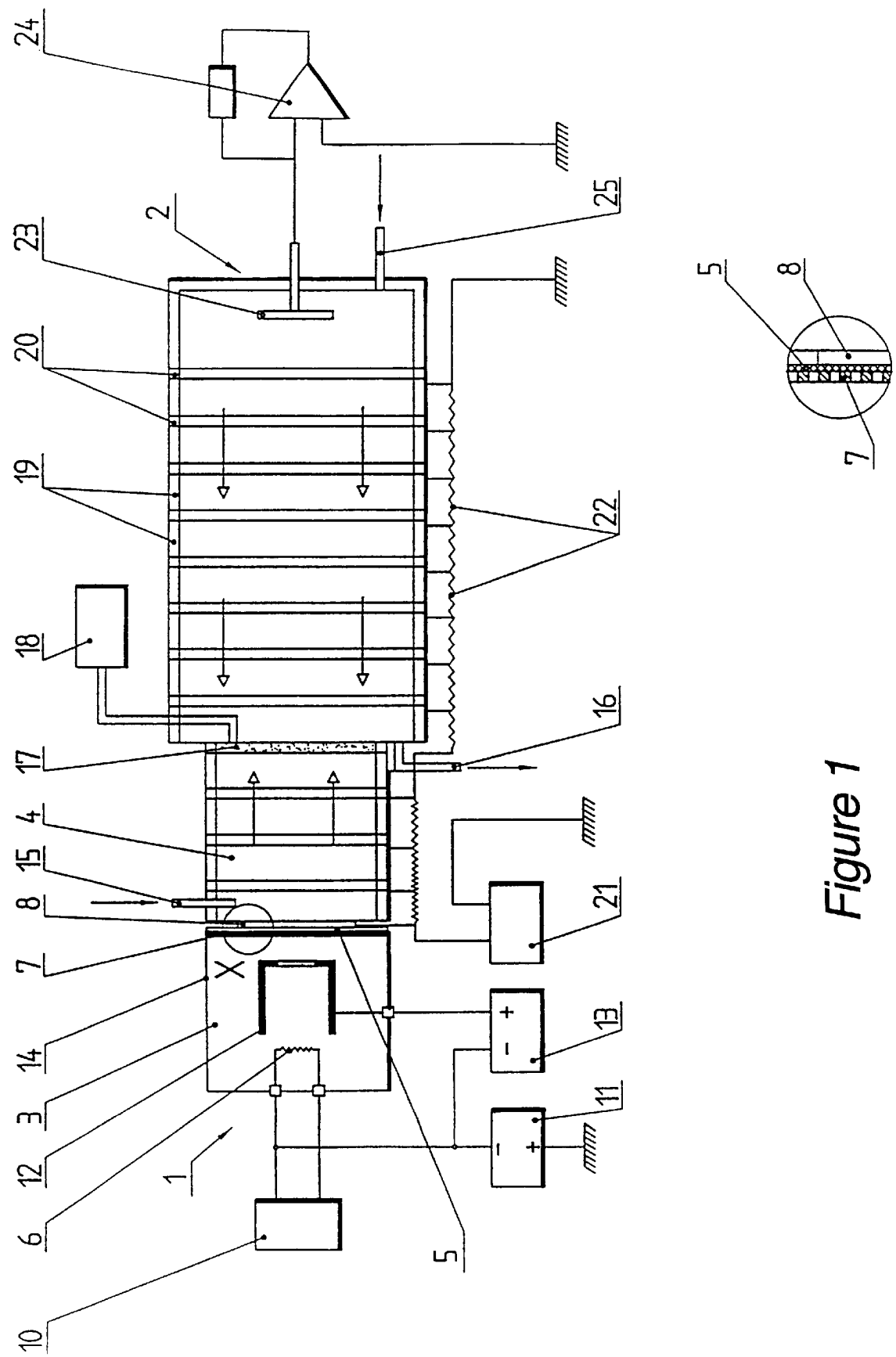
FIG. 1 a block diagram of the proposed spectrometer with a thermoemitter as an electron source.

The proposed IMS consists of a reaction chamber 1 and a drift chamber 2. The reaction chamber 1 is separated into two partial chambers 3 and 4 by a partition wall 5 made from material permeable to electrons and impermeable to gas, for example, mica. The inner volume of partial chamber 3 of the reaction chamber 1 is evacuated and a non-radioactive electron source 6 is mounted therein. In order to eliminate any bending due to the pressure difference between the parts 3 and 4 of reaction chamber 1, the partition wall 5 is supported by a metal grid 7 with a geometric transmission coefficient (ratio between open and covered surfaces) more than 60%. The thickness of said partition wall 5 is 3–5 microns. The surface of the partition wall 5 facing partial chamber 4 of said reaction chamber 1 is coated by a layer 8 of conductive material, for example aluminum. The thickness of said layer 8 is 0.03–0.05 microns. In one embodiment of the spectrometer according to FIG. 1, a thermoemitter 6 in the form of a tungsten spiral connected to a heater voltage source 10 is used as an electron source. The thermoemitter 6 is connected to a negative terminal of an accelerating voltage source 11 (20–30 kV). In the inner volume of partial chamber 3 of reaction chamber 1 there is an electron flow modulator 12 connected to a positive terminal of a voltage source 13. The casing 14 of partial chamber 3 of reaction chamber 1 is made from vacuum-tight material, for example, stainless steel or glass. Partial chamber 4 of reaction chamber 1 comprises an input 15 to supply analyte and an output 16 to withdraw this analyte. The inner volume of said partial chamber 4 of reaction chamber 1 is separated from the inner volume of drift chamber 2 by a shutter grid 17 connected to pulsed voltage source 18. The casing of partial chamber 4 of reaction chamber 1 and the casing of drift chamber 2 are formed by metal rings 19 separated by rings 20 made from electrically insulating material, for example, ceramics. The metal rings 19 are connected to a high DC voltage source 21 (0.5–3 kV) via a voltage divider 22. At the end of said drift chamber 2 opposite to the connection between chambers 1 and 2, a collecting electrode 23 connected to an electrometer 24 is mounted. Adjacent to the collecting electrode 23, a branch pipe 25 for supplying a drift gas is mounted. The surface of the partition wall 5 is coated by a layer 8 of conductive material which is connected to a positive terminal of the high DC voltage source 21.

In this embodiment the spectrometer operates in the following manner:

The spiral of thermoemitter 6, heated by a current from heater voltage source 10, emits electrons. The sources 11 and 13 produce a potential difference between the thermoemitter 6 and the additional accelerating electrode 12 which in its turn accelerates said electrons in the evacuated volume of partial chamber 3 of reaction chamber 1 towards partition wall 5; whereby these electrons receive energy sufficient for penetrating through said partition 5 into the second partial chamber 4 of reaction chamber 1. In the inner volume of the second partial chamber 4 of reaction chamber 1, the electrons interact with the molecules of a carrier gas and with the molecules of substance to be analyzed, that is supplied through the input 15 with a gas flow. Positive and negative ions (including the ions of substances to be analyzed) are formed in partial chamber 4 of reaction chamber 1 as a result of ion-molecule reactions. The high DC voltage source 21 generates an electric field under the action of which the ions (positive and negative, depending on polarity) move towards the shutter grid 17. Periodically short (0.1–5 μsec) voltage pulses are fed from source 18 to the shutter grid 17. These pulses generate ion packets that afterwards enter the inner volume of drift chamber 2. In the inner volume of drift chamber 2, the ions move against a flow of inert drift gas towards the collecting electrode 23 as a result of the action of the potential gradient induced by the voltage that is fed from a high-voltage source 21 via a divider 22 to the metal rings of the drift chamber tube. As they move towards the collecting electrode 23, the ions are separated due to the mobility differences of the various molecular ions. Arriving at the collecting electrode 23, the ions produce an electrical current that is amplified and measured by the electrometer 24.

Figure 2:
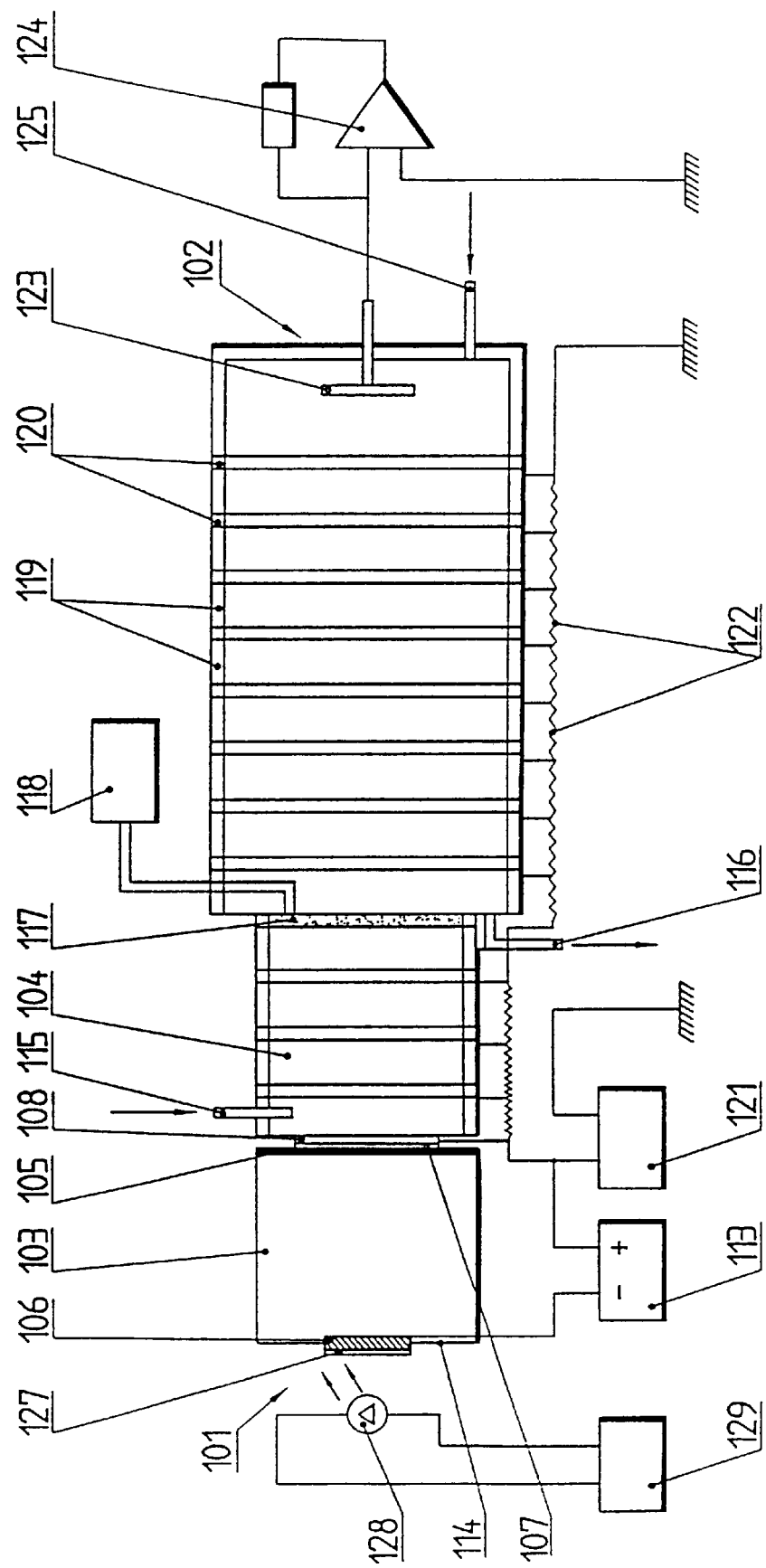
FIG. 2 a block diagram of the proposed spectrometer with a photocathode as an electron source.

The embodiment of FIG. 2 differs from the above-mentioned IMS in using a photocathode 106 (e.g. a multi-alkaline one) connected to a negative terminal of the accelerating voltage source 113, as a non-radioactive electron source 106. In the casing 114 of partial chamber 103 of reaction chamber 101, opposite to photocathode 106 there is a window 127 made from material transparent to radiation. Outside the casing 114 of partial chamber, opposite to window 127, a radiation source 128 connected to a voltage source 129 is mounted.

The radiation from source 128 passes through window 127, falls onto photocathode 106 and causes electron emission from its surface. The electrons are accelerated by the electric field produced by the accelerating voltage source 113, until they attain energy sufficient for penetrating through the partition wall 105 into the inner volume of partial chamber 104 of reaction chamber 101, where they interact with the molecules to be analyzed. The rest of the analysis and detection operations with respect to the ions separated in drift chamber 102 are similar to the procedures described in connection with the embodiment of FIG. 1. Reference numbers of corresponding components are obtained by adding 100 to the ones of FIG. 1.

The invention claimed is:

1. Ion mobility spectrometer with a reaction chamber, a drift chamber, a non-radioactive electron source mounted in the reaction chamber, an input to supply an analyte to the reaction chamber and an output to withdraw said analyte as well as a collecting electrode mounted in the drift chamber, wherein the reaction chamber is divided by a partition wall being permeable to electrons and impermeable to gas into a first partial chamber and a second partial chamber and, wherein the non-radioactive source is mounted in the first partial chamber, and the second partial chamber is connected to a gas input and output to supply and withdraw gas and wherein an inner volume of the first partial chamber is evacuated, and the electron source is connected to the negative terminal of an accelerating voltage source.

2. Ion mobility spectrometer according to claim 1, wherein the partition wall consists of mica.

3. Ion mobility spectrometer according to claim 1, wherein the partition wall is supported by a metal grid.

4. Ion mobility spectrometer according to claim 1, wherein the partition wall has a surface coated by a layer of conductive material which is connected to the positive terminal of an accelerating voltage source and facing the second partial chamber.

5. Ion mobility spectrometer according to claim 1, wherein the non-radioactive electron source comprises a thermoemitter supplied by a heater voltage source.

6. Ion mobility spectrometer according to claim 1, wherein the non-radioactive electron source comprises a photocathode, wherein a casing of the first partial chamber comprises a window made from material transparent to radiation and wherein a radiation source is mounted outside the reaction chamber opposite to said window.

7. Ion mobility spectrometer according to claim 1, wherein an additional accelerating electrode mounted between the electron source and the partition wall and connected to the accelerating voltage source.

8. Method to analyze impurities in a gas comprising:

providing a reaction chamber that is divided into two partial chambers by a partition wall that is permeable to electrons and impermeable to gas;

substantially evacuating an inner volume of the first partial chamber;

generating electrons with an electron source in the first partial chamber; and supplying and withdrawing said gas and impurities to and from the second partial chamber via a gas input and a gas output such that impurity molecules are ionized in the second partial chamber by electrons generated in the first chamber.

9. Ion mobility spectrometer with a reaction chamber, a drift chamber, a non-radioactive electron source mounted in the reaction chamber, an input to supply an analyte to the reaction chamber and an output to withdraw said analyte as well as a collecting electrode mounted in the drift chamber, wherein the reaction chamber is divided by a partition wall being permeable to electrons and impermeable to gas into two partial chambers and, wherein the non-radioactive source is mounted in the first partial chamber, and the second partial chamber is connected to a gas input and output to supply and withdraw gas and wherein the inner volume of the first partial chamber is evacuated, and the electron source is connected to the negative terminal of an accelerating voltage source, wherein the partition wall consists of mica, is supported by a metal grid and has a surface coated by a layer of conductive material which is connected to the positive terminal of an accelerating voltage source and facing the second partial chamber.

10. Ion mobility spectrometer according to claim 9, wherein the non-radioactive electron source comprises a thermoemitter supplied by a heater source voltage source.

11. Ion mobility spectrometer according to claim 10, wherein an additional accelerating electrode mounted between the electron source and the partition wall and connected to the accelerating voltage source.

12. Ion mobility spectrometer according to claim 9, wherein the non-radioactive electron source comprises a photocathode, wherein a casing of the first partial chamber comprises a window made from material transparent to radiation and wherein a radiation source is mounted outside the reaction chamber opposite to said window.

13. Ion mobility spectrometer according to claim 12, wherein an additional accelerating electrode mounted between the electron source and the partition wall and connected to the accelerating voltage source.

* * * * *